United States Patent [19]

Dollinger

[11] Patent Number: 5,451,505
[45] Date of Patent: Sep. 19, 1995

[54] METHODS FOR TAGGING AND TRACING MATERIALS WITH NUCLEIC ACIDS

[75] Inventor: Gavin D. Dollinger, San Francisco, Calif.

[73] Assignee: Hoffmann-La Roche Inc., Nutley, N.J.

[21] Appl. No.: 887,424

[22] Filed: May 21, 1992

Related U.S. Application Data

[63] Continuation of Ser. No. 355,445, May 22, 1989, abandoned.

[51] Int. Cl.$^6$ .................... C12Q 1/68; C07H 21/00
[52] U.S. Cl. ........................ 435/6; 436/501; 436/523; 436/528; 436/20; 436/56; 436/63; 435/91.1; 435/91.2; 935/77; 935/78; 935/88; 536/25.3
[58] Field of Search ............ 435/6, 91.1, 91.2; 436/518, 519, 523, 528, 174, 800, 804, 808, 63, 501, 30, 56; 935/77, 78; 536/25.3

[56] References Cited

U.S. PATENT DOCUMENTS

| | | | |
|---|---|---|---|
| 4,359,353 | 11/1982 | Kydd | 149/2 |
| 4,441,943 | 4/1984 | Kydd | 149/109 |
| 4,683,195 | 7/1987 | Mullis et al. | 435/6 |
| 4,683,202 | 7/1987 | Mullis | 435/91 |
| 4,786,600 | 11/1988 | Kramer et al. | 435/235 |
| 4,824,667 | 4/1989 | Kit et al. | 424/89 |
| 4,957,858 | 9/1990 | Chu et al. | 435/6 |

FOREIGN PATENT DOCUMENTS

| | | |
|---|---|---|
| 231608 | 8/1987 | European Pat. Off. |
| 258017 | 3/1988 | European Pat. Off. |
| 9002709 | of 0000 | WIPO |
| WO8706383 | 10/1987 | WIPO |

OTHER PUBLICATIONS

Chu et al. (1986) Nuc. Acids Res., vol. 14, No. 14, pp. 5591–5603.
Innis et al., *PCR Protocols;* Academic Press Inc., 1990, pp. 54–59.
Bodnar et al., J. Biol. Chem., Dec. 1983, p. 15206.
Kremsky et al., Nucelic Acids Research, vol. 15, No. 7, 1987, pp. 2891–2893.
Hames et al., *Nucleic Acid Hybridization,* IRL Press, Nov. 1985, pp. 86–87.
Alwine et al., Proc. Natl. Acad. Sci. USA, vol. 74, No. 12, Dec. 1977, pp. 5350–5354.
Biosis Abstract No. 84095817, Bisbal et al., Biochemistry, vol. 26, (16), 1987.
"First Use of Gene Transfer In Human Cancer Patient," *San Francisco Chronicle,* May 23, 1989.
"Brand New," *Scientific American,* Jun., 1986.

*Primary Examiner*—Margaret Parr
*Assistant Examiner*—Ardin H. Marschel
*Attorney, Agent, or Firm*—George M. Gould; Dennis P. Tramaloni; Stacey R. Sias

[57] ABSTRACT

The present invention provides methods for tagging and tracing materials using nucleic acids as taggants. The process of tagging involves altering a substance in a manner that allows for the subsequent identification of the substance by detecting the alteration. The alteration disclosed herein involves nucleic acids.

16 Claims, No Drawings

METHODS FOR TAGGING AND TRACING MATERIALS WITH NUCLEIC ACIDS

This application is a continuation of U.S. Pat. application No. 07/355,445, filed May 22, 1989 (now abandoned).

BACKGROUND OF THE INVENTION

1. Field of the Invention

The present invention provides methods for tagging and tracing materials using nucleic acids as taggants. The process of tagging involves altering a substance in a manner that allows for the subsequent identification of the substance by detecting the alteration. The alteration disclosed herein involves nucleic acids.

Society currently attempts to track the manufacture and distribution of a large number of diverse substances, including (1) natural resources such as animals, plants, oil, minerals, and water; (2) chemicals such as drugs, solvents, petroleum products, and explosives; (3) commercial by-products including pollutants such as radioactive or other hazardous waste; and (4) articles of manufacture such as guns, typewriters, automobiles and automobile parts. Tagging aids in the determination of product identity and so provides information useful to manufacturers and consumers.

Some of the diverse uses of tagging methods and reagents include the identification of the manufacturer of an explosive, even after detonation, and the determination of flow patterns, so as to measure the spread of pollutants. The present invention provides a significant advance in the field, because the taggants can encode substantial amounts of information to aid subsequent identification. Moreover, by using recently available amplification technology, one can detect far less taggant than ever before. In fact, the present tagging methods work with such vanishingly small levels of taggant that drugs tagged by the present method can still pass the FDA standards (10 pg/dose) for amount of DNA, in this case, taggant DNA, in any product.

2. Information Disclosure

The use of tagging substances with polypeptides is known. U.S. Pat. Nos. 4,359,353 and 4,441,943. As with the nucleic acid taggants of the subject invention, the polypeptide taggants use the order of amino acids in the polypeptide to encode information.

SUMMARY OF THE INVENTION

The present invention provides a method for tagging a material (any substance) by treating the material with a nucleic acid taggant so that said nucleic acid attaches to said material in an amount sufficient for subsequent detection. The nucleic acid taggant comprises a specific nucleotide sequence or has a distinct composition of specific nucleotides to facilitate tracing. The present invention also provides a method for tracing a material tagged with a nucleic acid taggant that comprises determining the presence of a nucleic acid sequence specific for said taggant in the material. In a preferred embodiment, the tracing method also comprises treating the material under conditions that would result in the amplification of a nucleic acid sequence of a taggant, if present, to determine if the specific nucleic acid sequence is present.

More particularly, this invention provides for a method of monitoring the presence of a substance which comprises tagging the substance with a nucleic acid, collecting Said substance and detecting said nucleic acid. An additional step of amplification of the nucleic acid is also described herein. This amplification is typically done prior to detection and is preferably achieved using polymerase chain reaction technology. The nucleic acids can be either naturally occurring or synthetically derived. Preferred synthetic nucleic acids are comprised of inosine bases or 7-deaza-2'-deoxyguanosine nucleotides.

The materials or substances of this invention include those selected from the group consisting of air pollutants, oils, aromatic compounds, explosive compositions, food stuffs, medicaments, inks, paper goods, and paint products. The nucleic acids can be optionally bound to a component of the tagged substance through a covalent bond. "Covalently bound to a component of the substance," means that the nucleic acids are covalently bound to the tagged material or component thereof. Where the material is comprised of different components such as different chemical compounds, the nucleic acid may be covalently bound to any one or all of the components.

The nucleic acids used as taggants may be free or they may be covalently bound to a solid support (such as latex beads, dextran or magnetic beads) which is then mixed with the material being tagged. Alternatively the nucleic acids may be encapsulated by polymeric substances (such as proteins) or by lipophilic compositions (such as liposomes).

This invention also provides methods for tagging substances wherein the method comprises the step of incorporating a nucleic acid onto the substance or into the substance. The preferred taggants and substances are as described above.

This invention also provides compositions of tagged substances where the taggant is a nucleic acid having a specific sequence of nucleotide bases for retrospective identification. Preferred compositions are those which comprise the nucleic acid and a substance selected from the group consisting of air pollutants, oils, aromatic compounds, explosive compositions, food stuffs, medicaments, inks, paper goods, and paint products. The nucleic acids can be synthetically derived, covalently bound to solid support, or encapsulated, as described above.

This invention also provides for kits for the detection of substances tagged with nucleic acids. Such kits can include nucleic acids for the detection of the taggants, for the amplification of the taggants and for use as taggants.

The following definitions are provided of the invention:

SUBSTANCE—a material that can be tagged and traced according to the method of the invention.

NUCLEIC ACID—a deoxyribonucleotide or ribonucleotide polymer in either single- or double-stranded form; modified nucleotides may comprise all or pan of the nucleic acid.

TAGGANT—a nucleic acid that comprises a specific nucleotide sequence or has a specific nucleotide composition, the specificity of said sequence or composition providing a means to store information. Taggants are typically non-biologically functioning in that they are not a pan of a functional nucleic acid sequence operating in a living cell. Those of skill will recognize that living organisms contain unique nucleic acid sequences either natural or artificially introduced. this invention is not meant to embrace these naturally occurring and biologically functional forms of taggants. Taggants are generally added to substances. They are not a functioning pan of the substance.

TAGGING—the process of treating a material with a composition, the taggant, for subsequent identification of the material by detection of the taggant.

TRACING—the process of determining the origin or source of a material.

DETAILED DESCRIPTION

This invention relates to the use of nucleic acids for monitoring, detecting and tracing substances released into the environment or released into the stream of commerce. The nucleic acids are used as an additive to tag such substances. The specifics of compounding the nucleic acid as a taggant and its subsequent recovery for analysis is dependent upon the specific substance into which the nucleic acid is being added. The following guidelines are offered.

Nucleic acids.

The nucleic acids for use in this invention can provide a limitless amount of information. By using combinations of universal sequences (accepted as industrial standards) and by varying levels of specific sequences, one can identify the type of generic product, the product's origin (company specific sequences), the lot or batch, and even provide an identifier for a unit of commerce.

The nucleic acids suitable for use in this invention include both natural and non-natural nucleic acids. They can be single or double stranded. Natural nucleic acids refer to polymers of either DNA or RNA including the 5 naturally occurring bases, adenine, thymine, guanine, cytosine and uracil.

Non-natural or synthetic nucleic acids can also be used in this invention. Synthetic nucleic acids in some instances have advantages over natural nucleic acids, e.g. in stability, solubility, etc. Some synthetic nucleotides are less likely to be degraded by nuclease activity, by chemically active substances or by environmental conditions such as heat or ultraviolet radiation. The use of non-natural nucleotides is limited only by their ability to be effectively detected by the selected detection means. For tagging methods using the preferred PCR technology, the synthetic nucleic acid must form duplexes with the primers and function as a template for the polymerases used in the procedure. Non-natural nucleic acids for use in this invention include those incorporating inosine bases, and derivatized nucleotides, such as 7-deaza-2'deoxyguanosine, methyl- (or longer alkyl-) phosphonate oligodeoxynucleotides, phosphorothioate oligodeoxynucleotides, and alpha-anomeric oligodeoxynucleotides.

The nucleic acids for use in this invention can provide a limitless amount of information. By using combinations of universal sequences (accepted as industrial standards) and by varying levels of specific sequences, one can identify or authenticate the type of generic product, the product's origin (company specific sequences) and the lot or batch.

Tagged Substances.

The following substances are not meant to be limiting, but will serve to offer those of skill an understanding of the versatility of this invention. For example, it is expected that this invention will find application in explosives (such as plastic explosives and gunpowder), aerosols (such as automobile or industrial pollutants from smoke stacks), organic solvents (such as from dry cleaners, chemical factories, airports, and gas stations), paper goods (such as newsprint, money, and legal documents), inks, perfumes, and pharmaceutical products (such as medicaments).

Preparation of the nucleic acids will vary in accordance with the nature of the substance and upon the expected impact of the environment in which the substance is expected to be placed. The substances can be classified as solids, liquids or gases. The substances can be either inert or active, with liquids and aerosols being further divided as being either polar or non-polar.

Inert solids such as paper, many pharmaceutical products, wood, some foodstuffs, or polymer compounds (e.g., plastics), can be processed with the taggant or the taggant can be sprayed onto the surface of the solid. Taggants can be physically mixed with inert liquids or gases.

Chemically active substances, such as foodstuffs with enzymatic activity, polymers with charged groups, or acidic pharmaceuticals may require that a protective composition be added to the nucleic acid taggants. Protective compositions would include substances which would encapsulate the nucleic acids and protect them from enzymatic or chemical degradation. Liposomes are a technology presently available for use as a protective capsule for nucleic acids. Typical liposomes are micelle bodies formed by detergents. Alternatively polymeric substances can be used to electrostatically bind to and encapsulate the nucleic acids. Polymeric substances would include proteins such as virus coat proteins.

The same approach is used for the addition of taggants to chemically active liquids except the protective composition for a liquid is preferably compatible with the liquid's polarity. The compatibility of taggant with a liquid substance is preferred for both inert and chemically active liquids. For example, oils and other non-polar liquids can be tagged effectively by the use of detergents added to the taggant prior to the addition of the taggant to the liquid. One could rely upon Brownian motion to ensure a uniform distribution in the liquid.

For gases, the taggants are simply mixed with the gas. This is because the taggant is much smaller that what is usually considered to be dust (0.2 microns) particles. Containerized gases would have the taggants placed in the container. For gases being released into the atmosphere, the taggants could be mixed before release or at the time of release. For example, to track the pattern of dispersal of gases released by industry, one could attach an aerosol delivery device to an exhaust outlet and introduce a metered mount of taggant as the gas is released.

The use of nucleic acid taggants for the tracing of radioactive products, including waste, is anticipated. The means for tracing would be as described herein for non-radioactive materials with the use of appropriate protection. It should be noted that short oligonucleotides of less than 1000 bases are preferred due to their greater stability against degradation from radiation.

Recovery and detection of taggants.

The amount to add to a substance and preferred means for recovery and detection of nucleic acid taggant is dependent upon the substance being monitored. The means for detection and the amount of available sample being collected will dictate the amount of taggant required for each application of this invention.

Therefore, in the absence of a means to amplify the taggant, the amount of taggant added would depend on the logistics of collecting enough substance to recover a detectable amount of taggant.

The preferred molecular structure of the nucleic acid taggant will vary-with the means used to detect the nucleic acid. Typically at least 20 bases are necessary to ensure adequate specificity for any taggant so that accidental contamination will not lead to false results. Preferably, the sequence should comprise multiple regions of specificity. The longer the sequence, the more information may be carded. However, it will be recognized that the higher the information content of the taggant the more likely that degradation will be become a problem. Typically, fragments under 1 kilobase are preferred.

Recovery of the taggant can be achieved by the use of standard techniques. Typically, the sample is washed or extracted with either distilled water or a buffered solution. Physiological pH is preferred as pH extremes may degrade nucleic acid. Charged substances might require washing in high molarity salt buffers to act as ion exchangers with the electrostatically bound nucleic acids. Detergents, either ionic or non-ionic, are helpful to remove nucleic acids from surfaces or from complex biological mixtures. Using phenol based extractions or phenol/chloroform extractions, one can recover nucleic acid from complex biological substances or from oil based substances.

The recovered nucleic acid can be concentrated by standard techniques such as precipitation with alcohol, evaporation, or microfiltration.

Because of the limits of sensitivity for the detection of nucleic acid, there is an obvious advantage to using methods for amplifying the recovered taggant. For example, using the polymerase chain reaction procedure [PCR] disclosed in U.S. Pat. Nos. 4,683,202 and 4,683,195 and European Patent Applications Nos. 258,017 and 237,362, one can amplify and detect nucleic acid molecule. The PCR method can be used with modification to amplify single stranded taggants, double stranded taggants and DNA or RNA taggants.

Those of skill in the art recognize that the PCR amplification can be carried out in a variety of ways. For instance, inverse PCR and asymetric PCR are well known variations of the technique. In another variation, promoters for RNA transcription can be incorporated into primers, which, when extended and replicated by PCR, can then be used to create RNA copies of the target sequence. These RNA copies can, in turn, be several reverse transcribed into DNA, which can then be amplified by PCR. As with all PCR processes, reaction cycles can be repeated as often as desired.

For PCR, the preferred means for amplification, a double stranded taggant is preferred, although a single stranded taggant becomes a double stranded after the first cycle of amplification. The taggant is preferably a minimum of 60 bases long. This permits the hybridization of two primers which are preferably each 20 bases long, and which, when hybridized to the taggant, are separated by an internal region between the primer specific regions of the taggant of about an additional 20 bases.

When detecting nucleic acid by PCR, prior knowledge of the target sequence is necessary to provide appropriate primers. This necessary knowledge offers a valuable degree of security for those who desire it. For without the primers which can remain proprietary, the taggant can be virtually undetectable.

For detection of taggants, one can use standard nucleic acid hybridization assays or nucleic acid sequencing. The standard nucleic acid hybridization assays include single phase and mixed phase assays such as sandwich assays.

The specific detection procedure used is not critical to this invention. Nucleic acid hybridization technology is not a static art. New developments are anticipated and this invention is applicable to any new improvements. An overview of the state of the art can be found in Nucleic Acid Hybridization A Practical Approach, Eds. Hames, B. D. and Higgins, S. J., IRL Press, Wash. D.C., 1987.

The use of nucleic acid hybridization assays requires prior knowledge of the sequence being detected. Knowledge of the taggant's sequence permits the use of appropriate complementary oligonucleotides for capture or signal purposes.

Alternatively, the nucleic acids recovered from the samples can be sequenced using conventional sequencing technology. Commercially available kits are suitable for this purpose. The basic sequencing technology is derived from seminal references such as the Maxam and Gilbert procedure for DNA sequencing described in Methods in Enzymology 65:(part 1) 497–559. Sequencing is a more difficult procedure to conduct, but offers greater reliability than nucleic acid hybridization assays. This is due to the possibility of contamination by extraneous nucleic acid with sufficient complementarity to hybridize to the selected probes and offer false positives. Kits.

This invention also provides for a manufactured product such as a kit designed to tag and monitor substances. Such a kit would include nucleic acid taggants and polynucleotides which are complementary to the taggants. The complementary polynucleotides could be designed for use as signal probes, capture probes or as primers in the PCR method. The kits might also contain signal means such as enzymes, radio-isotopes, fluorescent labels and the like.

All cited references are provided for the convenience of the readers. The knowledge contained therein is well known to those of skill in the art. To the extent that such knowledge may be deemed essential to practice this invention, each of the above-cited references is hereby incorporated by reference.

The following examples are provided for illustrative purposes only and they are not to be interpreted as limitations of the invention.

Examples

The following examples all used a double stranded taggant of a sequence complementary to the DQα allele 1.3. This sequence is derived from a rare DQα type and has a reduced likelihood of being accidently present as a contaminant in the materials described below. The taggant was also labelled with $^{32}P$ to follow experimentally the tag during the entire procedure. The unique sequence of one strand of this taggant has been provided in Table 1.

The taggant was recovered as described below. All amplifications were done with 40 cycles on a Perkins-Elmer Cetus Instruments thermal cycler using the protocols and reagents provided by the manufacturer. Biotinylated primers GH26 and GH27 having the sequence provided in Table 1 were used to initiate the PCR process.

TABLE 1

Nucleic acid sequences for DHα, related primers and probes.

GH26 - 5' GTGCTGCAGGTGTAAACTTGTACCAG 3'
GH27 - 5' CACGGATCCGGTAGCAGCGGTAGAGTTG 3'
Taggant sequence DQα -
5' TTTTACGGTCCCTCTGGCCAGTTCACCCATGAATTTGATGGAGATGAG
CAGTTCTACGTGGACCTGGAGAAGAAGGAGACTGCCTGGCGGTGGCCTGAGT
TCAGCAAATTTGGAGGTTTTGACCCGCAGGGTGCACTGAGAAACATGGCTGT
GGCAAAACACAACTTGAACATCATGATTAAACGCTA 3'
Capture probe GH89 5' - CTGGAGAAGAAGGAGAC - 3'

The Standard PCR procedure.

The following PCR procedure was used to amplify DQα in each of the different substances illustrated below.

The basic PCR mixture consists of:

| 10x TAQ buffer | | 10 μl |
| --- | --- | --- |
| 100 mM | Tris HCl pH 8.3 | |
| 500 mM | KCl | |
| 15.0 mM | MgCl$_2$ | |
| 10 μM GH26 | | 1.5 μl |
| 10 μM GH27 | | 1.5 μl |
| 100 mM dNTPs | | 0.75 μl |
| 5 U/μl TAQ | | 0.5 μl |
| distilled water | | 35 μl |

50μl of the basic PCR mixture is mixed with an equal amount of sample. Each cycle consists of 30 second incubations at 94° C. followed by 30 sec at 55° C. and 30 sec at 72° C. After the final (fortieth) cycle, the sample mixture is incubated at 72° C. for ten minutes.

Detection of the PCR amplified taggant is achieved by standard nucleic acid hybridization assays using the capture probe provided in Table 1. The protocol for the hybridization assay is not critical. The means used in our laboratory have been detailed in U.S. Ser. No. 197,000, filed May 20, 1988, and the CIP of that application, Ser. No. 347,495, filed May 4, 1989, which are hereby incorporated by reference. Briefly, the taggant was captured by hybridization to an immobilized probe, GH89 (table 1 ). The probe was immobilized using ultraviolet irradiation on a positively charged nylon membrane.

A. Gunpowder

Preparation: (a) Add 16 ng of taggant to 1 ml of distilled water; (b) mix solution with 1 g of nitrocellulose based gunpowder, and (c) dry in air or under vacuum a 85° C.

Recovery: (a) Wash gunpowder with distilled water (1 ml); (b) add 50 μl of this solution to PCR reaction mix or place gunpowder flakes directly in 100 μl PCR reaction mix; and (c) amplify.

B. Oil

Preparation: (a) Mix together 40 μg of taggant, 10 μl "Tween 80" (detergent), 10 μl "Span 80" (detergent), and 100 μl distilled water; and (b) add mixture to 1.7 ml oil. The combination is then thoroughly mixed.

Recovery: Add oil directly to PCR mix, vortex and amplify; or use a standard phenol-chloroform extraction. After treatment with phenol, the taggant was detected in the boundary layer between the oil and water phases.

C. Medicines (water soluble tablets)

Preparation: (a) Add 48 μg of taggant to 325 μl of distilled water; (b) add 50 μl of this mix to a tablet; and (c) allow to dry.

Recovery: (a) dissolve the tablet in 5 ml of H$_2$O; (b) place 50 μl of this solution in PCR mix; and (c) amplify.

D. Ink p

Preparation: If water insoluble, mix with detergents as for tagging oil. If water soluble, add a dilute concentration of taggant directly to the ink.

Recovery: As described for oils and medicines.

E. Paper goods

Preparation: (a) Add dilute solution of taggant 2–3 ng/cm$_2$ to paper; and (b) allow to air dry or dry under vacuum.

Recovery: (a) Soak paper in distilled water with or without detergents to aid in solubilization; (b) optionally concentrate taggant; and (c) amplify by standard PCR procedure.

F. Food Stuffs

Preparation: Add 20 ng taggant to each gram of food by physical mixing or spray application.

Recovery: (a) Food material is washed with distilled water; (b) the rinse is optionally concentrated; and (c) the rinse material is subjected to the standard PCR procedure.

What is claimed is:

1. A method of monitoring the presence of a substance exposed to naturally occurring ultraviolet radiation which comprises tagging the substance with a nucleic acid of at least 20 and less than 1,000 nucleotides, releasing the tagged substance in a manner exposing said substance and nucleic acid to naturally occurring ultraviolet radiation, collecting the nucleic acid, amplifying said nucleic acid using the polymerase chain reaction, and monitoring the presence of the substance by detecting the amplified product of said nucleic acid.

2. A method of claim 1 wherein the nucleic acid is non-natural nucleic acid comprising inosine bases or derivatized nucleotides selected from the group consisting of 7-deaza-2'deoxyguanosine, alkyl-phosphonate oligodeoxy-nucleotides, phosphorothioate oligodeoxynucleotides, and alpha-anomeric oligonucleotides.

3. A method of claim 1 wherein the nucleic acid comprises a derivatized nucleotide.

4. A method of claim 1 where the substance is selected from the group consisting of air pollutants, oils, aromatic compounds, explosive compositions, food stuffs, medicaments, inks, paper goods, and paint products.

5. A method of claim 4 wherein the nucleic acid is covalently bound to a component of the substance.

6. A method of claim 4 wherein the nucleic acid is covalently bound to a solid support.

7. A method of claim 4 wherein the nucleic acid is encapsulated by a lipophilic composition.

8. A method of claim 4 wherein the nucleic acid is encapsulated by a polymeric composition.

9. A method of claim 1 wherein the substance is tagged with a nucleic acid having two predetermined subsequences, the first identifying a genera of substances, and the second identifying a subgenera of substances.

10. A method of tagging a substance comprising the step of incorporating a non-natural nucleic acid having a specific sequence of nucleotide bases for retrospective identification into or onto the substance wherein the non-natural nucleic acid is exposed to naturally occurring ultraviolet radiation and is at least 20 nucleotides and less than 1000 nucleotides and further comprises inosine bases or derivatized necleotides selected from the group consisting of 7-deaza-2'deoxyguanosine, alkyl-phosphonate oligodeoxy-nucleotides, phosphorothioate oligodeoxynucleotides, and alpha-anomeric oligodeoxynucleotides.

11. A method claim 10 where the substance is selected from the group consisting of air pollutants, oil, aromatic compounds, explosive compositions, food stuffs, medicaments, inks, paper goods, and paint products.

12. A method of claim 11 wherein the nucleic acid is covalently bound to a component of the substance.

13. A method of claim 11 wherein the nucleic acid is covalently bound to a solid support.

14. A method of claim 11 wherein the nucleic acid is encapsulated by a lipophilic composition.

15. A method of monitoring the presence or absence of a substance which comprises tagging the substance with a nucleic acid of at least 20 and less than 1,000 nucleotides, releasing the substance and nucleic acid, collecting the nucleic acid, amplifying said nucleic acid, and monitoring the presence or absence of the substance by detecting the presence or absence of the amplified product of said nucleic acid wherein the nucleic acid when released with the substance is not sealed collectively in a container and is exposed to the atmosphere.

16. A method of monitoring the presence or absence of a substance which comprises tagging the substance with a nucleic acid of at least 20 and less than 1,000 nucleotides, releasing the substance, collecting the nucleic acid, amplifying said nucleic acid, and monitoring the presence or absence of the substance by detecting the presence or absence of the amplified product of said nucleic acid wherein the nucleic acid when released with the substance is not sealed collectively in a container and is exposed to the atmosphere and wherein the substance is selected from the group consisting of air pollutants, oil, aromatic compounds, explosive compositions, food stuffs, medicaments, inks, paper goods and paint products.

* * * * *